United States Patent [19]

Allard et al.

[11] Patent Number: 5,496,319
[45] Date of Patent: Mar. 5, 1996

[54] EXTERNAL FIXATION APPARATUS

[75] Inventors: Randall N. Allard, Plymouth; Gregory G. Price; Gary T. Hamman, both of Warsaw; Billy N. Sisk, Claypool, all of Ind.

[73] Assignee: Zimmer, Inc., Warsaw, Ind.

[21] Appl. No.: 266,917

[22] Filed: Jun. 27, 1994

[51] Int. Cl.⁶ .......................... A61B 17/62; A61B 17/66
[52] U.S. Cl. ................................ 606/56; 606/54; 606/57; 606/59; 403/4
[58] Field of Search .................. 606/53, 54, 55, 606/56, 57, 58, 59, 60, 61, 69, 70, 71, 90, 96, 105; 403/3, 4

[56] References Cited

U.S. PATENT DOCUMENTS

| | | |
|---|---|---|
| 4,308,863 | 1/1982 | Fischer . |
| 4,365,624 | 12/1982 | Jaquet . |
| 4,535,763 | 8/1985 | Jaquet . |
| 4,620,533 | 11/1986 | Mears . |
| 4,624,249 | 11/1986 | Alvarez Cambras . |
| 4,693,240 | 9/1987 | Evans ........................................ 606/54 |
| 4,768,524 | 9/1988 | Hardy . |
| 4,784,125 | 11/1988 | Monticelli et al. . |
| 4,889,111 | 12/1989 | Ben-Dov . |
| 4,920,959 | 5/1990 | Witzel et al. ............................. 606/53 |
| 4,923,458 | 5/1990 | Fischer ..................................... 606/59 |
| 4,936,843 | 6/1990 | Sohngen ................................... 606/54 |
| 4,941,481 | 7/1990 | Wagenknecht ........................... 606/59 |
| 5,021,054 | 6/1991 | Monfardini et al. ..................... 606/54 |
| 5,067,954 | 11/1991 | Ilizarov ................................... 606/58 |
| 5,087,258 | 2/1992 | Schewior ................................. 606/56 |
| 5,095,919 | 3/1992 | Monticelli et al. ...................... 606/56 |
| 5,098,432 | 3/1992 | Wagenknecht ........................... 606/54 |
| 5,112,331 | 5/1992 | Miletich .................................. 606/53 |
| 5,167,661 | 12/1992 | Wagenknecht ........................... 606/54 |
| 5,209,751 | 5/1993 | Farris et al. ............................. 606/61 |
| 5,275,598 | 1/1994 | Cook ....................................... 606/54 |

FOREIGN PATENT DOCUMENTS 2499400  8/1982  France .

OTHER PUBLICATIONS

Zimmer, Inc.—Brochure—Torus External Fixation System—Lit. No. 97-2613-01 Rev. 1—1993.

*Primary Examiner*—Stephen C. Pellegrino
*Assistant Examiner*—Scott B. Markow
*Attorney, Agent, or Firm*—Margaret L. Geringer

[57] ABSTRACT

An external fixation apparatus 2 that allows the transfixation wire 10 to be secured at a plurality of discrete positions to provide adjustability of the angular orientation of the wire with respect to the plane of a frame ring 6. The fixation apparatus 2 includes a transfixation wire or pin 10 that is connected between a transmitting clamp 20 and a receiving clamp 40 that are shiftably carried atop of a partial frame ring 6. A wire retainer 50 is secured to the distal end 14 of the transfixation wire. The receiving clamp 40 includes a raised member 46 adapted for receiving distal end 14 of wire 10 and mating with retainer 50 at a variety of discrete positions along the length of raised member 46. Retainer 50 uses two screws 54, 56 to secure distal end 14 of wire 10 within a longitudinal through bore 51. Screw 54 extends into longitudinal bore 51 to engage wire 10 near the proximal end of retainer 50. Screw 56 extends into longitudinal bore 51 and bends the distal end 14 of wire 10 downward within a slot 53 defined along longitudinal bore 51 at the distal end of retainer 50. Bending the distal end 14 of wire 10 within retainer 50 improves the connection between wire 10 and retainer 50.

7 Claims, 8 Drawing Sheets

# EXTERNAL FIXATION APPARATUS

This invention relates to an external fixation apparatus for stabilizing a bone and has specific relevance to an external fixation apparatus having improved securement and adjustability of the transfixation wires.

BACKGROUND OF INVENTION

External fixation devices or fixators are well known in the field of orthopedic medicine. External fixators are used to support and align a fractured bone to facilitate healing. An external fixator such as the Torus™ External Fixation System manufactured by Zimmer, Inc., includes an external frame of interconnected bars and partial rings secured to the bone by both transfixating and non-transfixating pins and wires. Transfixating wires and pins pass laterally through the bone and are connected at opposite ends to the frame.

Once the transfixation wire is inserted through the bone and tissue, small adjustments to the alignment and attitude of the frame with respect to the bone are often desirable. Such adjustments, however, often require removing, realigning and reattaching components to the bone. Such attaching and reattaching can result in increased trauma to the bone tissue. It is advantageous to allow for angular adjustment of the transfixation wires to ensure the alignment and position of the frame without increasing tissue trauma.

SUMMARY OF INVENTION

The external fixation apparatus of this invention allows the transfixation wire to be secured at a plurality of discrete positions to provide adjustability to the angular orientation of the wire with respect to the plane of the ring. The external fixation apparatus of this invention includes a transfixation wire or pin that is connected between a transmitting clamp and a receiving clamp that are shiftably carried atop a partial frame ring. A wire retainer is secured to the distal end of the transfixation wire. The receiving clamp includes a raised member adapted for receiving the distal end of the transfixation wire and mating with the retainer at a variety of discrete positions along the length of the raised member.

In one embodiment, the receiving clamp includes a raised member or back having a longitudinal opening for receiving the distal end of the transfixation wire. A plurality of lateral slots are formed in the raised member along the side of the longitudinal opening. The retainer includes a flange which engages one set of slots to angularly position the wire when the transfixation wire is tensioned. In an alterative embodiment, the receiving clamp includes a raised member or back having a plurality of staggered bores for receiving the transfixation wire. The transfixation wire can be inserted through one of the holes to properly position the partial ring and properly align the fixation apparatus with respect to the body or extremity.

The retainer of this invention provides increased securement between the wire and the receiving clamp. The retainer has a longitudinal bore for receiving the distal end of the transfixation wire. Two screws are used to secure the wire within the longitudinal bore. One screw extends into the longitudinal bore to engage the wire near the proximal end of the retainer. The other screw extends into the longitudinal bore and bends the distal end of the wire downward within a slot defined along the longitudinal bore at the distal end of the retainer. Bending the transfixation wire within the retainer improves the connection between the transfixation wire and the retainer.

Accordingly, an advantage of this invention is to provide for an external fixation apparatus with improved adjustability.

Another advantage of this invention is to provide for an external fixation apparatus including a transfixation wire that is connected between a transmitting clamp and receiving clamp in a variety of discrete positions to provide for adjustability of the angular orientation of the wire with respect to the external ring or frame.

Another advantage of this invention is to provide a receiving clamp and retainer secured to the distal end of the transfixation wire to be cooperatively mated in a variety of discrete positions to provide for adjustability of the angular orientation of the wire with respect to the external ring or frame.

Another advantage of this invention is to provide an external fixation apparatus with an improved wire or pin retainer that bends the transfixation wire within the retainer to increase the holding power.

Other advantages will become apparent upon a reading of the following description.

BRIEF DESCRIPTION OF THE DRAWINGS

A preferred embodiment of the invention has been depicted for illustrative purposes only wherein.

DESCRIPTION OF THE PREFERRED EMBODIMENT

The preferred embodiments herein described are not intended to be exhaustive or to limit the invention to the precise form disclosed. They are chosen and described to explain the principles of the invention and its application and practical use to enable others skilled in the art to utilize its teachings.

Figure 1:
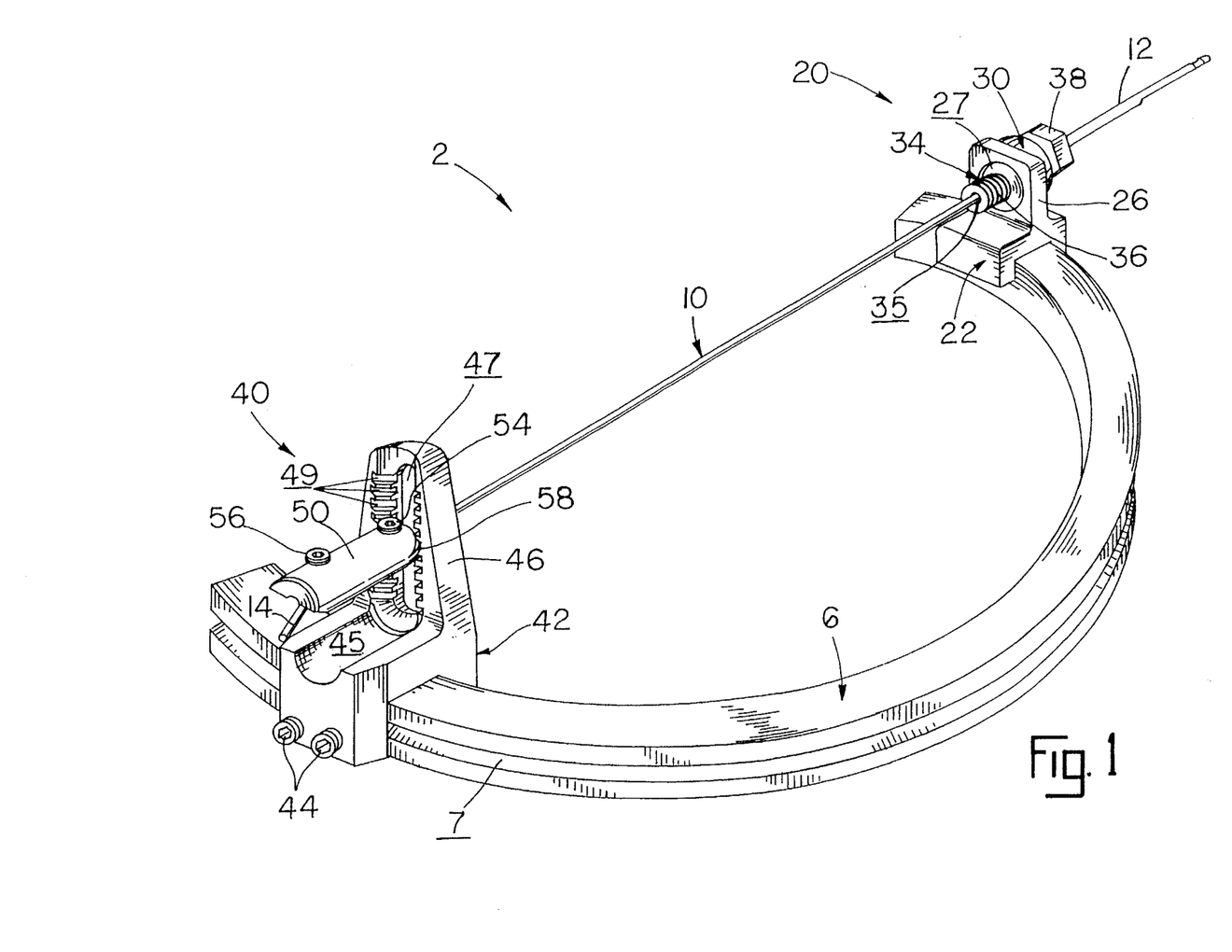
FIG. 1 is a perspective view of the fixation apparatus of this invention.
Figure 11:
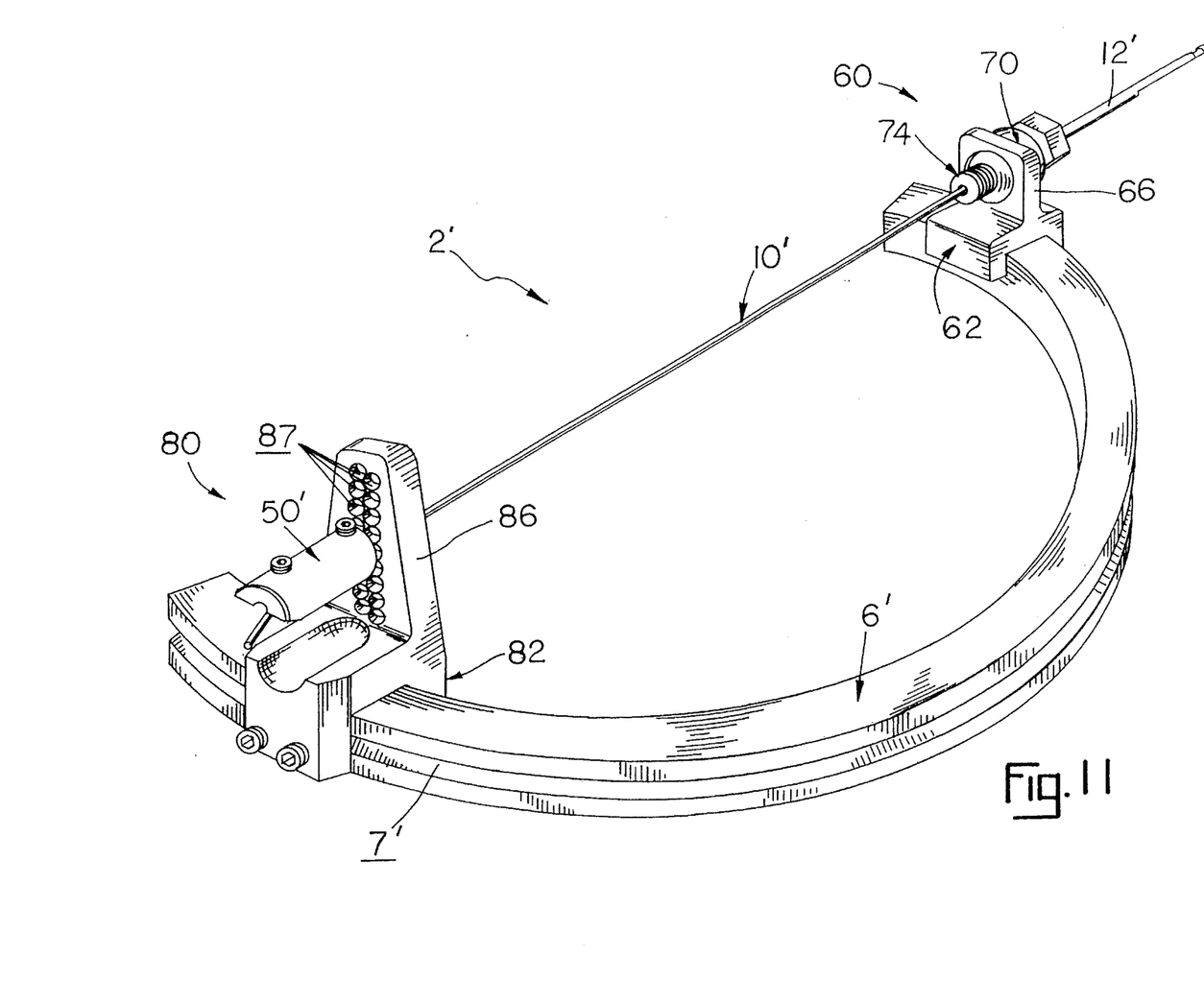
FIG. 11 is a perspective view of a second embodiment of the receiving clamp and retainer with the connected transfixation wire.

FIG. 1 shows one embodiment of the external fixation apparatus or fixator 2 of this invention. FIG. 11 shows a second embodiment of the external fixator of this invention. Both embodiments of the external fixators are similar in structure and basic operation. Preferably, components of both embodiments of the external fixators of this invention are constructed of titanium or other suitable material.

External fixator 2 includes a transfixation pin or wire 10 connected to a partial ring 6 by two shiftable fixation clamps 20, 40. Ring 6 provides part of an external frame for supporting a variety of fixation components such as additional rings, interconnecting bars, buttress pins and fixation pins and wires. Ring 6 has a generally planar parallel top and bottom surface and curved inner and outer surfaces. A V-shaped groove 7 is formed in the outer surface of ring 6 for engaging set screws operatively disposed in the fixation clamps 20, 40, although any suitable attachment mechanism may be used to secure the clamps to the ring. Transfixation pin or wire 10 is preferably an elongated titanium or stainless steel rod. The primary diameter of the wire 10 may be about 2.8 mm, although any suitable diameter may be utilized. Wire 10 has a proximal end 12 adapted for connection to a drill or similar device (not shown). The outer diameter of wire 10 is slightly greater at proximal end 12 which forms a shoulder 13. The distal end of wire 10 includes a suitable tapered drill tip 15 (shown in FIG. 8) which acts as a drill for inserting the wire through the bone stock and surrounding tissue. This drill tip 15 is subsequently nipped off to prevent injuries leaving a blunt distal end 14.

Figures 2, 3, 4:
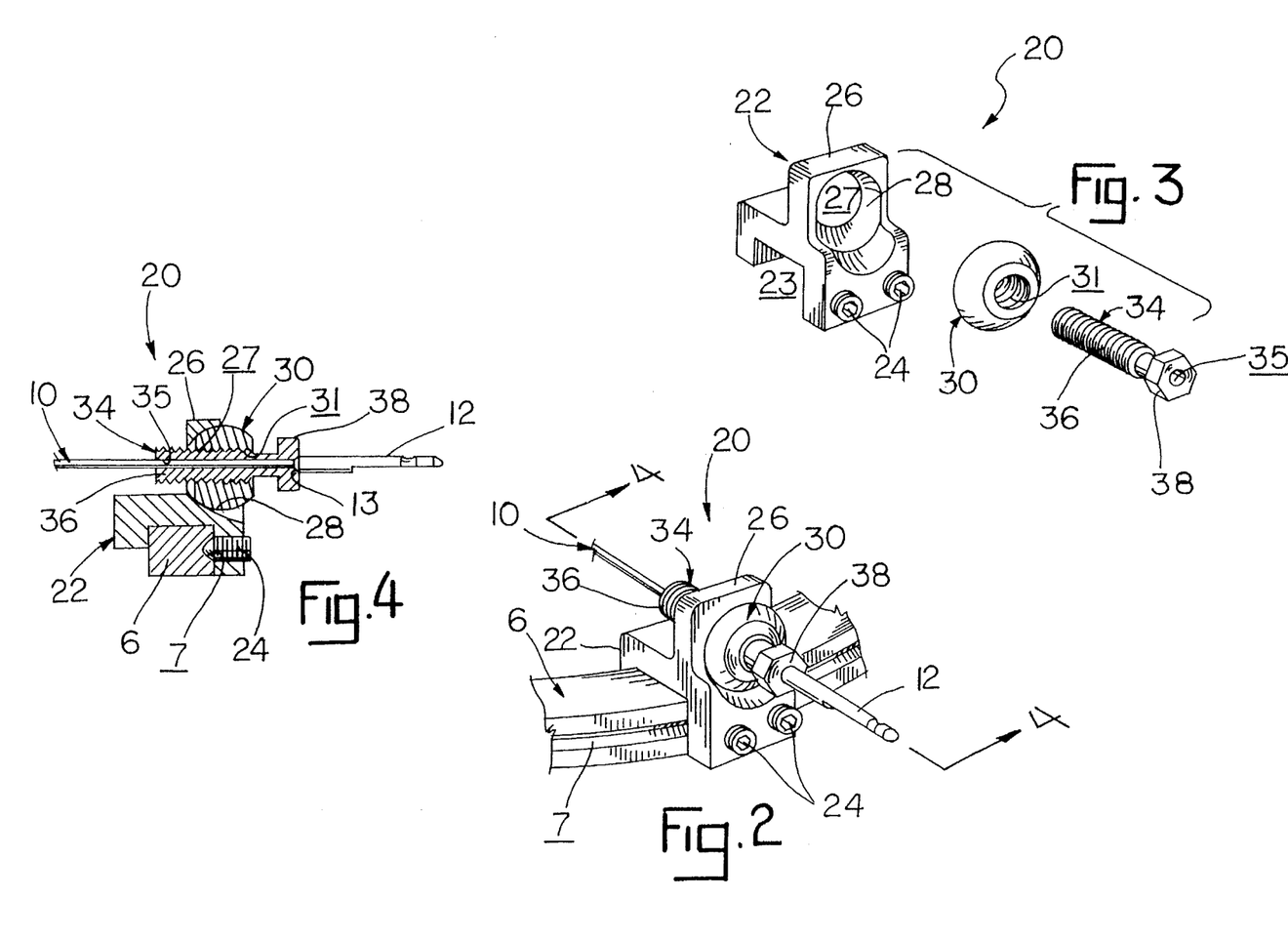
FIG. 2 is a perspective view of one embodiment of the transmitting clamp connecting the transfixation wire to a partial frame ring.
FIG. 3 is an exploded view of the transmitting clamp of FIG. 2 showing the clamp body, collet and tensioning bolt.
FIG. 4 is a sectional view of the transmitting clamp taken along line 4—4 of FIG. 2.

FIGS. 2–4 show transmitting clamp 20. Transmitting clamp 20 includes a clamp body 22, a collet 30, and a tension bolt 34. Clamp body 22 is shaped generally as shown in FIGS. 3 and has a lateral channel 23 defined in its lower surface. As shown in FIG. 2, clamp body 22 is shiftably mounted atop ring 6 with ring 6 seated within channel 23. A pair of screws 24 are turned into thread bores in clamp body 22 which extend into channel 23. Screws 24 seat within V-groove 7 of ring 6 to secure clamp body 22 to the ring. By tightening or loosening screws 24, clamp 20 can be positioned at any point along the length of the ring.

Clamp body 22 also includes a raised member 26 having a circular opening 27. Raised member 26 has a concave outer edge 28 around opening 27 which forms a seat for collet 30. Collet 30 has a threaded through bore 31. Tension bolt 34 includes a threaded shaft 36 and a hexagonal end 38. A longitudinal bore 35 extends the entire length of bolt 34 for receiving wire 10. As shown in FIGS. 2 and 4, collet 30 is seated within opening 27 and tensioning bolt 34 is turned into collet bore 35, such that bolt shaft 36 passes through opening 27 of raised member 26.

Figure 5:
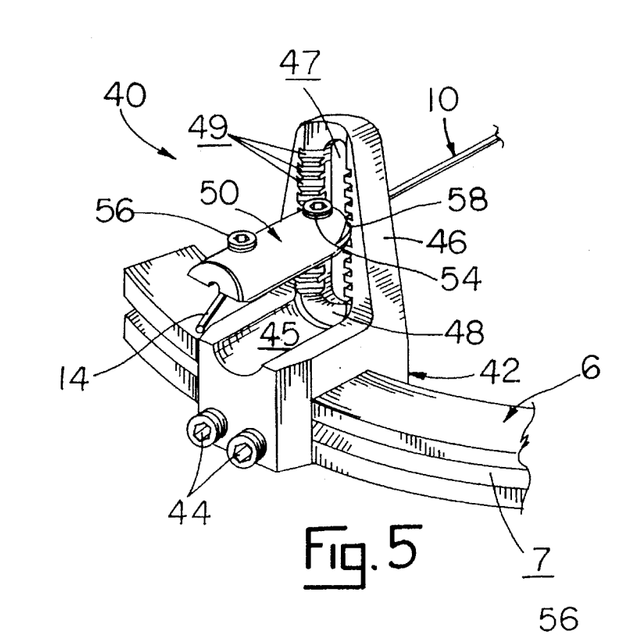
FIG. 5 is a perspective view of one embodiment of the receiving clamp and retainer with the connected transfixation wire.
Figure 6:
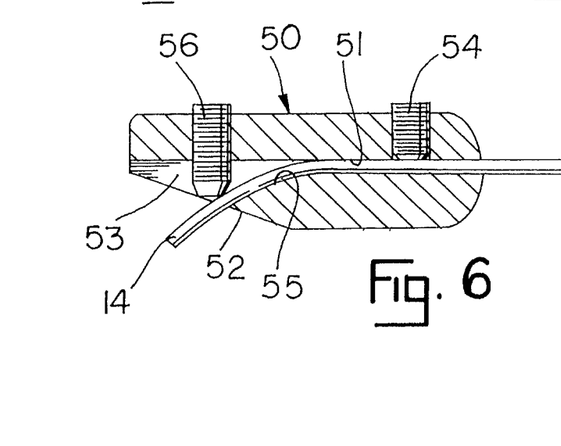
FIG. 6 is a sectional view of the retainer.

As shown in FIG. 5, receiving clamp 40 includes a clamp body 42 and a separate wire retainer 50. FIG. 6 shows a cross section of wire retainer 50. Wire retainer 50 has a longitudinal bore 51 extending the length of the retainer for receiving the distal end of wire 10. The distal end of bore 51 widens into a slot 53 defined by the chamfered lower surface 52 and the downwardly extending inner edge 55 of retainer 50. Two screws 54, 56 are turned into threaded bores that extend laterally into longitudinal bore 51. As shown in FIG. 6, screw 54 extends into the proximal end of longitudinal bore 51 to restrictively engage wire 10, and screw 56 extends into the distal end of longitudinal bore 51 to bend the wire downward into slot 53. As screw 56 is turned into its bore, wire 10 is bent along the curved inner edge 55 of retainer 50. The bend in wire 10 provides increased securement between the retainer and the transfixation wire. As shown in FIG. 5, two side flanges 58 protrude from the proximal end of retainer 50.

Figure 7:
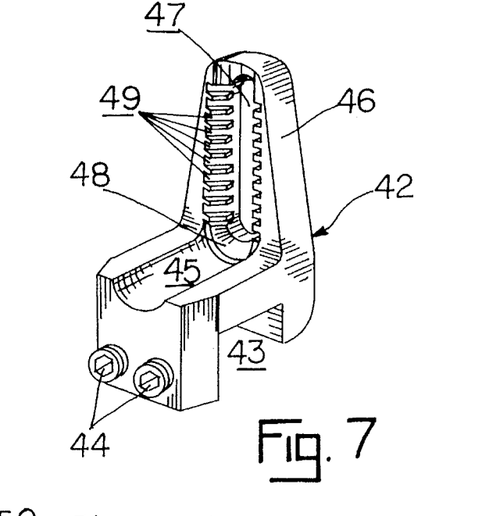
FIG. 7 is a perspective view of the receiving clamp of FIG. 1.

Clamp body 42 is shaped generally as shown in FIG. 7 and has a lateral channel 43 defined in its lower surface. As shown in FIG. 5, clamp body 42 is shiftably carried atop ring 6 with ring 6 seated within channel 43. A pair of screws 44 are turned into thread bores in clamp body 42 which extend into channel 43. Screws 44 seat within V-groove 7 of ring 6 to secure clamp body 42 to ring 6. By tightening or loosening screws 44, receiving clamp 40 can be positioned at any point along the length of the partial ring. As shown in FIGS. 5 and 6, clamp body 42 also includes a raised member 46 having a longitudinal opening 47. Raised member 46 has a concave outer receiving edge 48 around opening 47 which forms a seat for the proximal end of retainer 50. A plurality of paired lateral slots 49 are formed along both sides of receiving edge 48.

As shown in FIG. 5, the proximal end of retainer 50 abuts against receiving edge 48. When wire 10 is tensioned by tensioning bolt 34, side flanges 58 of retainer 50 are fitted within one of the paired slots 49 formed along receiving edge 48. Slots 49 provide a variety of discrete positions along the length of raised member 46 in which retainer 50 can be seated for adjusting the angular orientation of wire 10 with respect to ring 6. Consequently, retainer 50 can be selectively secured between an upper position shown in FIG. 9 and a lower position shown in FIG. 10. It should be noted that in the lower position, wire 10 is substantially parallel with the plane of ring 6. A trough 45 is formed in the upper surface of clamp body 42 to receive retainer 50 when the retainer is secured at its lowest position.

The wire or pin 10 can be adjusted up to 21 mm in height on the receiver clamp end of the wire, or up to a total angulation of 8°, depending on the size of the ring 6. These adjustment amounts are identified as representative of the amount of adjustment or wire alignment flexibility potentially avilable with the present invention; however, these amounts are not intended to be limiting. It is understood that the design can be adapted to provide varying degrees of adjustability.

Figure 8:
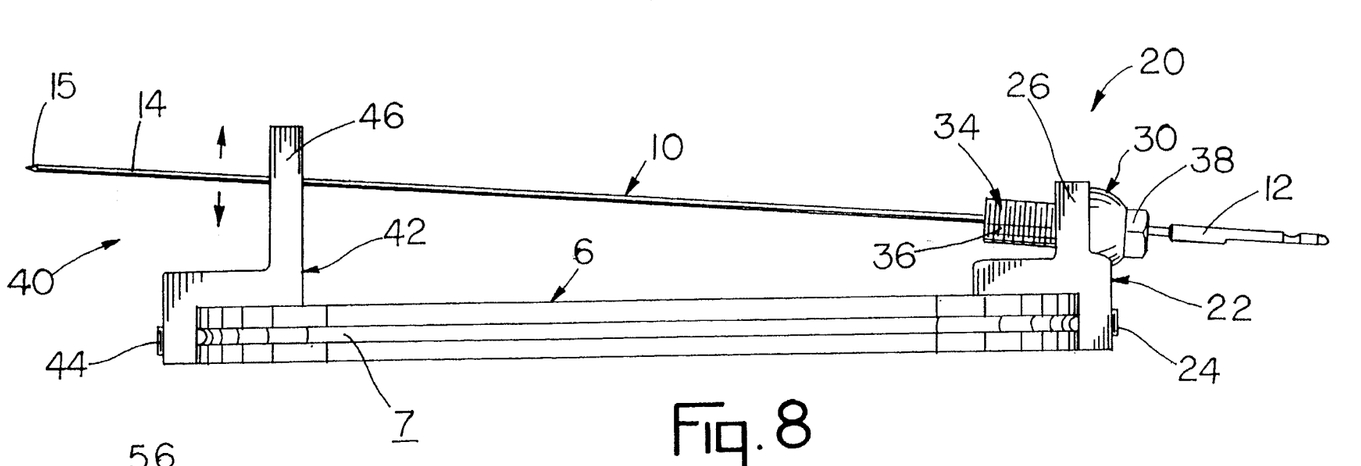
FIG. 8 is a side view of the fixation apparatus of FIG. 1 showing angular adjustability of the retainer when the tension bolt is turned into the collet to loosen the transfixation wire.
Figure 9:
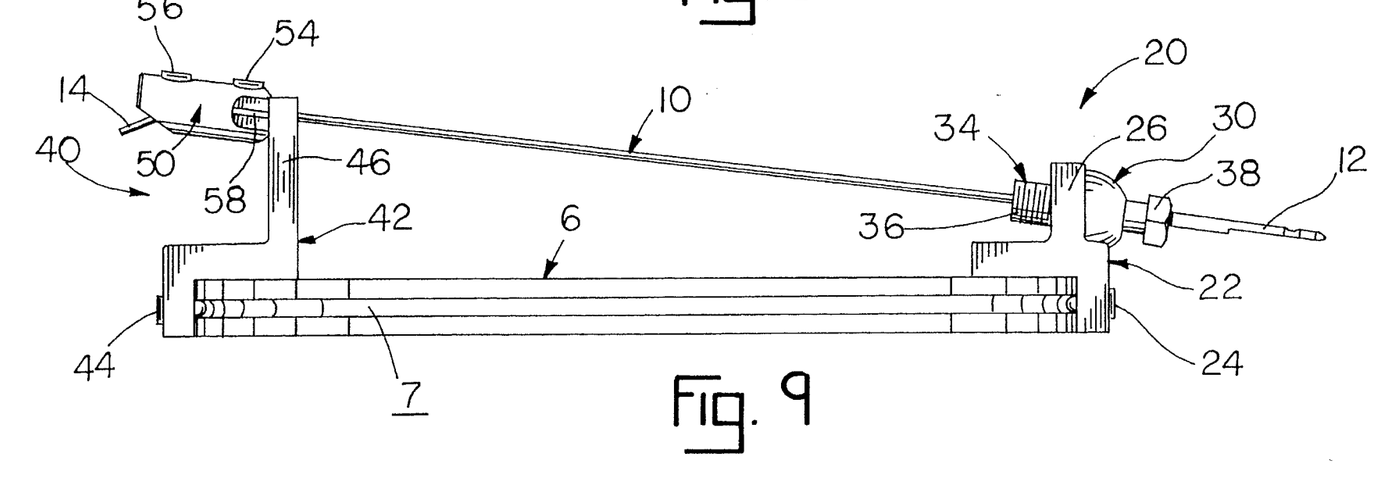
FIG. 9 is a side view of the fixation apparatus of FIG. 1 showing the retainer and transfixation wire positioned at the upper extremity of the receiving clamp.
Figure 10:
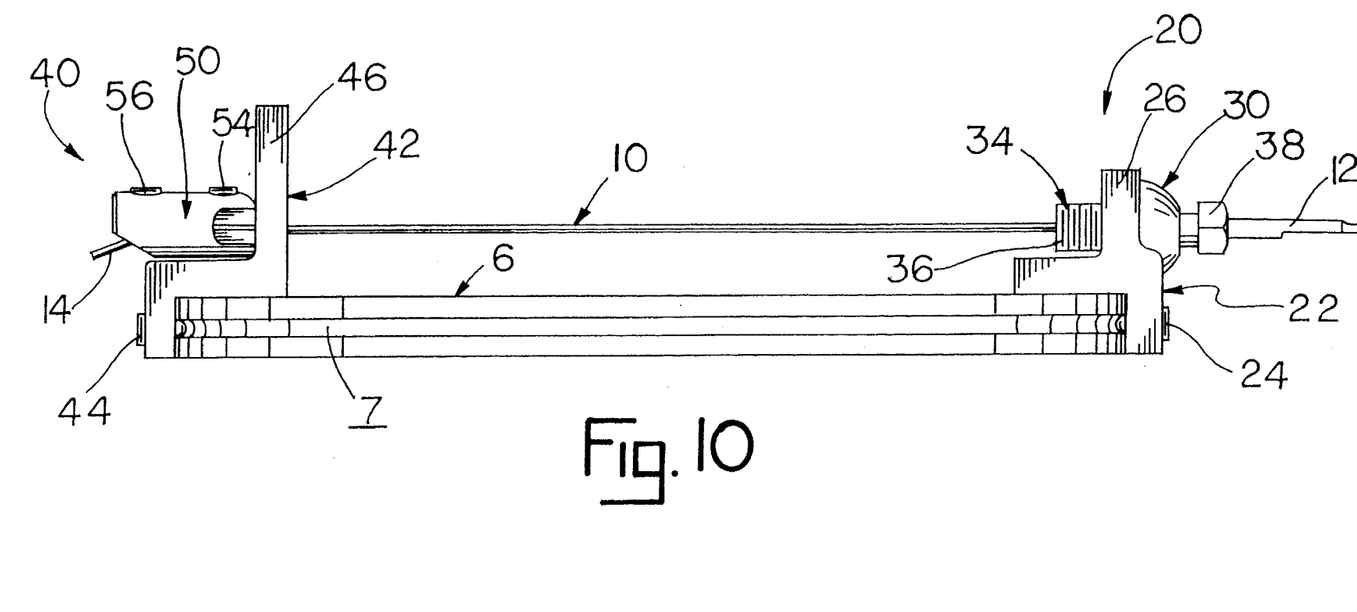
FIG. 10 is a side view of the fixation apparatus of FIG. 1 showing the retainer and the transfixation wire positioned at a lower extremity of the receiving clamp.

FIGS. 8–10 illustrate the placement and adjustability of fixator 2. Ring 6 is positioned around the body extremity (not shown). Proximal end 12 of transfixation wire 10 is connected to a drill device (not shown) and the distal end of the wire is inserted through tension bolt 34. As shown in FIG. 8, tension bolt 34 is turned substantially into collet 30 to allow for maximum adjustability and tensioning. The wire 10 with the bolt 34 and collet 30 assembly thereon is inserted through opening 27 in transmitter clamp 20 until collet 30 engages opening 27. Wire 10 is then drilled laterally through the bone and surrounding tissue. The transmitter clamp 20 is then loosely mounted to ring 6. The receiver clamp 40 is then slid over the distal end of wire 10 via opening 47 of receiving clamp 40, and receiver clamp 40 is attached to ring 6. Confirm the positioning of clamps 20,40, and tighten the respective clamp set screws to secure the proper clamp position. Alignment of wire 10 within receiving clamp 40 is a resultant of wire 10 being inserted by the surgeon. The variety of discrete positions available on clamp 40 by slots 49 provides angular flexibility for insertion of the wire 10 by the surgeon. Retainer 50 is slipped over distal end of wire 10 until the flange 58 of retainer 50 engages the appropriate slot 49 in receiver clamp 40. Lock screws 54, 56 are drawn down to secure and bend the distal end of wire 10 into an interlocking engagement within retainer 50. The drill tip 15 is typically cut off after the wire 10 has been bent over by set screw 56 of retainer 50, leaving a blunt distal end 14.

Once retainer 50 is secured to the distal end of wire 10 and retainer 50 is properly seated within one of the slots 49 of clamp 40, tension bolt 34 is adjusted to draw wire 10 taut between clamps 20, 40. Drawing the pin taut also secures retainer 50 in engagement against raised member 46. As shown in FIG. 4, hex end 38 of bolt 34 abuts against shoulder 13 of pin 10. As hex end 38 of tension bolt 34 is rotated away from collet 30, hex end 38 urges proximal end 12 of pin 10 outward to draw pin 10 taut.

Typically, two transfixation wires 10 may be utilized on the ring 6, each connected to the ring via a respective transmitter and receiver clamp. To properly adjust the tension on the transfixation wires a wire tensioning socket (not shown) is attached to an in-line torque wrench (not shown). The socket is inserted over the hex end 38 of tensioning bolt 34 and tightened to about 1.0 to 1.4 Newton-meters. The distal end 14 of each wire 10 is cut flush with wire retainer 50 and the proximal end 12 Is cut close to the tensioning bolt using wire cutters (not shown). The wire ends are typically covered with protective covers (not shown).

FIG. 11 illustrates a second embodiment of an external fixator 2' of this invention. Fixator 2' is similar in structure and operation as fixator 2 described above. Fixator 2' includes a transfixation pin or wire 10' connected to a partial ring 6' by two shiftable fixation clamps 60, 80.

Figures 12, 13:
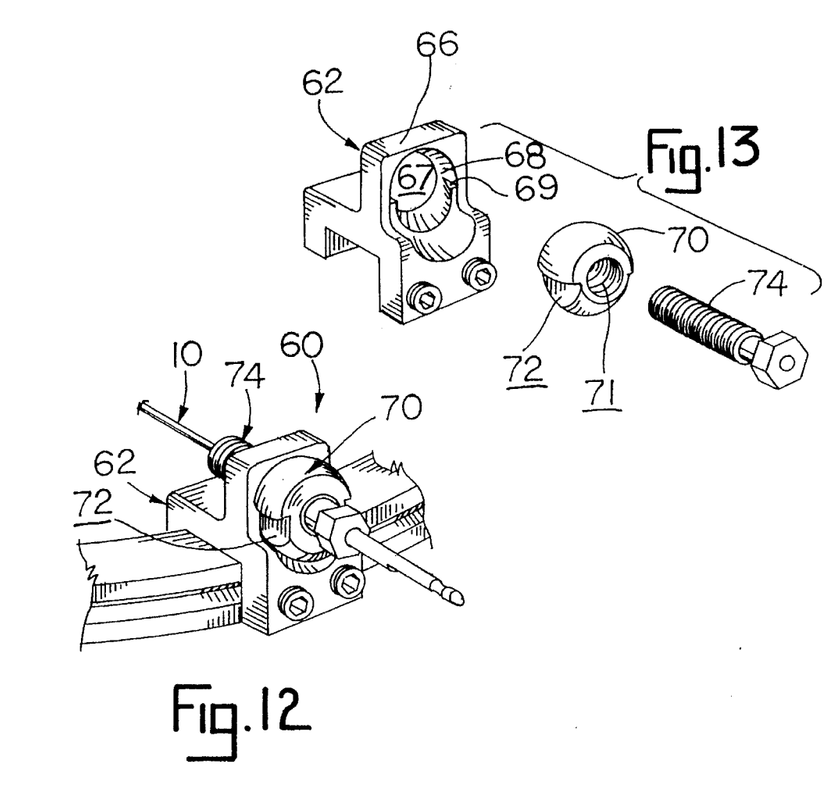
FIG. 12 is a perspective view of a second embodiment of the transmitting clamp connecting the transfixation wire to a partial frame ring.
FIG. 13 is an exploded view of the transmitting clamp of FIG. 12 showing the clamp body, collet and tension bolt.

FIGS. 12 and 13 show a second preferred embodiment of transmitting clamp 60. Transmitting clamp 60 is similar in structure and operation to transmitting clamp 20 described above. Transmitting clamp 60 includes a clamp body 62, a collet 70, and a tension bolt 74. Clamp body 62 is shaped generally as shown in FIGS. 12 and includes a raised member 66 having a circular opening 67. Raised member 66 has a concave outer edge 68 around opening 67 which forms a seat for collet 70. Two side tabs 69 protrude from edge 68. Collet 70 has a threaded through bore 71 and has two lateral notches 72 formed on opposite sides which abut against tabs 69 to act as a stop to prevent the collet from rotating about the axis of through bore 71 when the transfixation wire is tensioned by the rotatable adjustment of tension bolt 74. Collet 70 still allows some pivoting and tilting for adjustment of the angle of the wire prior to being tensioned or tightened in position.

Figure 14:
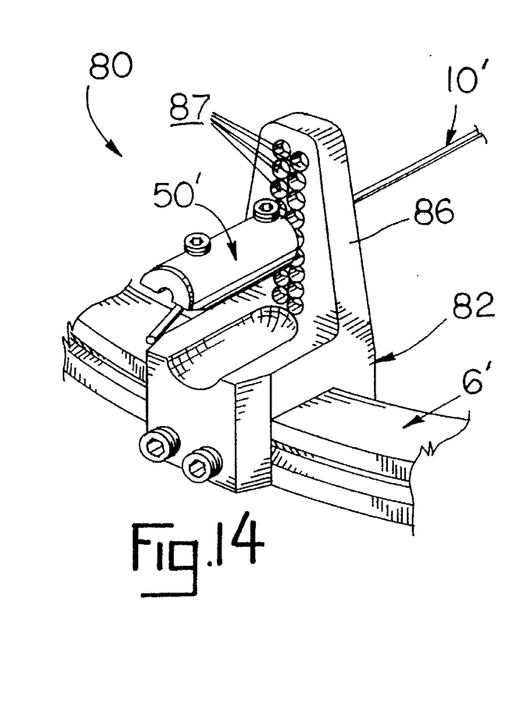
FIG. 14 is a perspective view of a second embodiment of the receiving clamp connecting the transfixation wire to a partial frame ring.
Figure 15:
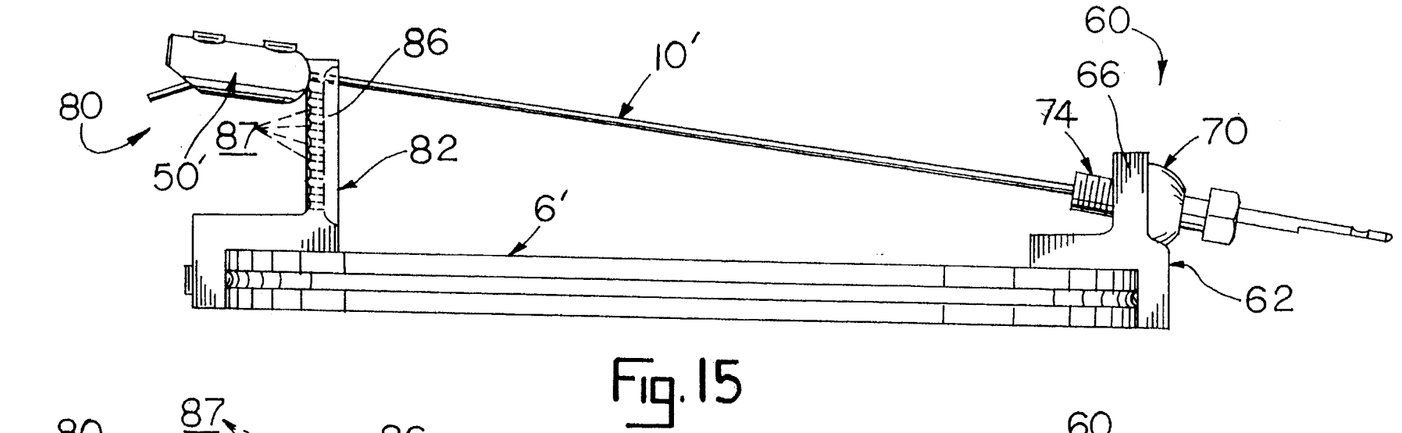
FIG. 15 is a sectional view of fixation apparatus of FIG. 11 showing the transfixation wire inserted through the upper most bore of the receiving clamp.
Figure 16:
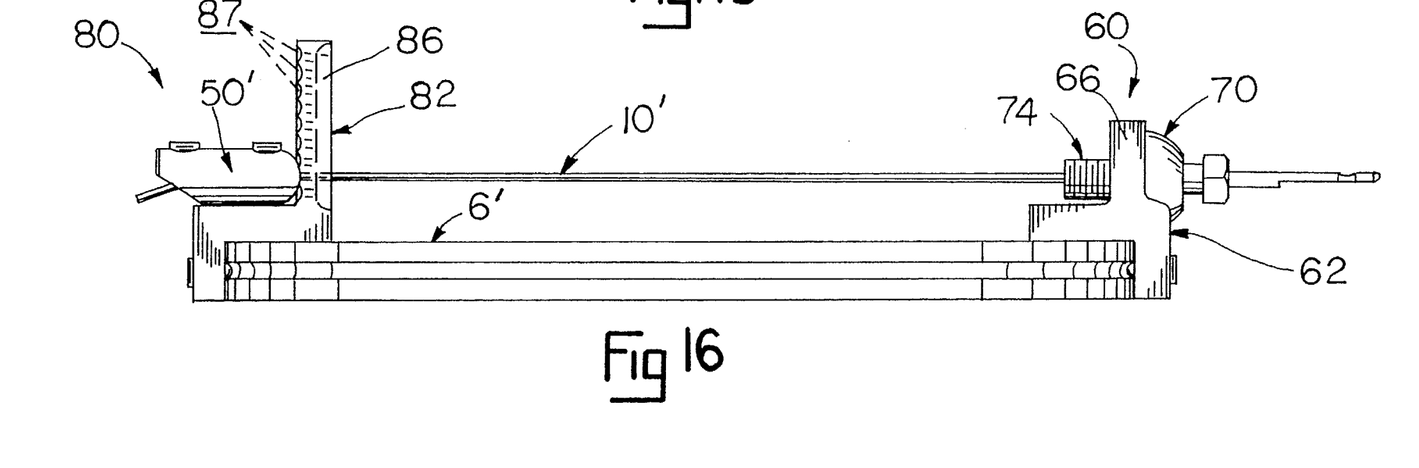
FIG. 16 is a sectional view of the fixation apparatus of FIG. 11 showing the transfixation wire inserted through a lower bore in the receiving clamp.

FIG. 14 shows a second embodiment of the receiving clamp 80 that includes a clamp body 82 and a separate wire retainer 50'. Receiving clamp 80 and retainer 50' are similar in structure to receiving clamp 40 and retainer 50 described above. Clamp body 82 is shaped generally as shown in FIGS. 14 and includes a raised member 86 having a plurality of bores 87 formed through raised member 86 and staggered along its medial axis. Bores 87 provide a variety of discrete positions along the length of raised member 86 in which the transfixation wire 10' can be inserted. As shown in FIG. 14, wire 10' is inserted through one of the bores and the rounded proximal end of retainer 50' abuts against raised member 86. FIG. 15 shows wire 10' inserted through the upper most bore 87 and FIG. 16 shows the wire inserted through a lower bore 87.

It is understood that the above description does not limit the invention to the details given, but may be modified within the scope of the following claims.

I claim:

1. An external bone fixation apparatus comprising:

a frame part adapted to overlie a body extremity, said frame part having a first one end and a second other end, a transfixation wire adapted for lateral insertion through said bone and having a proximal end and a distal end, a first clamp shiftably carried by said frame part for pivotally connecting said wire proximal end to one end of said frame part, second clamp shiftably carried by said frame part for connecting said wire distal end to the other end of said frame part, means carried by said first clamp for tensioning said wire between said first clamp and said second clamp, and means carried by said second clamp for providing adjustability of the angular orientation of said wire with respect to said frame part between a plurality of discrete positions wherein said adjustability means includes a raised member extending from said second clamp, said raised member having a first surface facing toward said first clamp and an oppositely facing second surface with an opening means extending through said raised member from the first surface to the second surface, and wherein said adjustability means further includes a wire retainer part connected to said wire distal end, said wire distal end extends through said opening means wherein said retainer part abuts against said oppositely facing second surface of said raised member when said wire is tensioned between said first and second clamp by said tensioning means, and wherein said opening means extending through said raised member is a continuous longitudinal opening defined therein, and wherein said longitudinal opening has a length and includes the plurality of discrete positions along the length of said continuous longitudinal opening on said second surface, and wherein said retainer part is seated against said second surface at a selected one of the plurality of discrete positions when said wire is tensioned between said first and second clamp, and wherein said raised member also has a plurality of parallel slots defined along at least a one side of the longitudinal opening on said second surface, said retainer part includes a flange, said flange is seated within one of said slots to secure the position of said retainer part along said longitudinal opening when said wire is tensioned between said first clamp and said second clamp.

2. An external bone fixation apparatus comprising:

a frame part adapted to overlie a body extremity, said frame part having a first one end and a second other end, a transfixation wire adapted for lateral insertion through said bone and having a proximal end and a distal end, a first clamp shiftably carried by said frame part for pivotally connecting said wire proximal end to one end of said frame part, second clamp shiftably carried by said frame part for connecting said wire distal end to the other end of said frame part, means carried by said first clamp for tensioning said wire between said first clamp and said second clamp, and means carried by said second clamp for providing adjustability of the angular orientation of said wire with respect to said frame part between a plurality of discrete positions, wherein said tensioning means includes a collet having a lateral bore and a bolt extensibly fitted into said collet bore, said bolt having a longitudinal through bore adapted for receiving said wire, said first clamp has an opening, said collet is seated within said first clamp opening, said wire extends through said bolt bore with said wire proximal end abutting said bolt whereby extensible movement of said bolt from said collet urges said wire proximal end away from said collet to tension said wire between said first clamp and said second clamp, and wherein said collet bore is threaded for rotatably receiving said bolt, said first clamp also includes a tab protruding into said first clamp opening, said collet has a notch formed along its side, said tab abutting said collet notch to prevent said collet from rotating within said first clamp opening when said bolt is rotated within said collet bore.

3. In combination, an apparatus and a transfixation wire, said apparatus for securing the transfixation wire to an external bone fixation device comprising:

a retainer part having a longitudinal bore extending between a proximal end and a distal end of said retainer part, said bore adapted for receiving a wire distal end, and means carried by said retainer part for bending said wire distal end within said retainer part to secure said wire distal end to said retainer part and wherein said bending means includes an extensible screw partially extending laterally into said longitudinal bore wherein said screw forcefully engages said wire distal end to bend said wire distal end within said longitudinal bore, and wherein a distal end of said bore widens into a slot to enable the wire to be bent downward into said slot, said slot extending from said bore outwardly, such that said bore is larger at the distal end of the retainer part than the proximal end of the retainer part.

4. The apparatus of claim 3 wherein said slot extends from said longitudinal bore outwardly to an outer surface of said retainer part.

5. The apparatus of claim 3 wherein said retainer part further includes a second screw for restrictively engaging the wire in the longitudinal bore.

6. An external bone fixation device comprising a fixation clamp and a fixation wire, said clamp used to connect one end of said fixation wire to a frame part, said fixation clamp adapted for providing adjustability of the angular orientation of said wire with respect to said frame part between a plurality of discrete positions and comprising:

a clamp body adapted for connecting to said frame part, a raised member extending from said clamp body, said raised member having a first surface and an oppositely facing second surface with a continuous longitudinal opening extending through said raised member from the first surface to the second surface, the longitudinal opening has a length and includes the plurality of discrete positions along the length of the opening, and a separate wire retainer part adapted for connection to said wire, said wire extends through said longitudinal opening wherein said retainer part is connected to said wire and seated against said second surface of said raised member at a selected one of the plurality of discrete positions along the length of said continuous longitudinal opening when said wire is secured to said fixation clamp, and wherein said raised member also has a plurality of slots defined along at least a one side of the longitudinal opening on said second surface, said retainer part includes a flange, said flange is seated within one of said slots to secure the position of said retainer part along said longitudinal opening when said wire is secured to said fixation clamp.

7. An external bone fixation apparatus comprising:

a frame part adapted to overlie a body extremity, said frame part having a first one end and a second other end, a transfixation wire adapted for lateral insertion through said bone and having a proximal end and a distal end, a first clamp shiftably carried by said frame part for pivotally connecting said wire proximal end to one end of said frame part, second clamp shiftably carried by said frame part for connecting said wire distal end to the other end of said frame part, means carried by said first clamp for tensioning said wire between said first clamp and said second clamp, and means carried by said second clamp for providing adjustability of the angular orientation of said wire with respect to said frame part between a plurality of discrete positions, and wherein said tensioning means includes a collet having a lateral bore and a bolt extensibly fitted into said collet bore, said bolt having a longitudinal through bore adapted for receiving said wire, said first clamp has an opening, said collet is seated within said first clamp opening, said wire extends through said bolt bore with an enlarged shoulder on said wire proximal end abutting said bolt whereby extensible movement of said bolt from said collet urges said wire proximal end away from said collet to tension said wire between said first clamp and said second clamp.

* * * * *